US010744270B2

(12) United States Patent
Avery et al.

(10) Patent No.: US 10,744,270 B2
(45) Date of Patent: Aug. 18, 2020

(54) DOSE SETTING MECHANISM AND DRUG DELIVERY DEVICE WITH RATCHET MECHANISM

(71) Applicant: Sanofi, Paris (FR)

(72) Inventors: Richard James Vincent Avery, Warwick (GB); Matthew Meredith Jones, Warwick (GB); William Geoffrey Arthur Marsh, Warwick (GB); Anthony Paul Morris, Warwick (GB); David Aubrey Plumptre, Warwick (GB); Samuel Keir Steel, Warwick (GB); Robert Frederick Veasey, Warwick (GB)

(73) Assignee: Sanofi, Paris (FR)

( * ) Notice: Subject to any disclaimer, the term of this patent is extended or adjusted under 35 U.S.C. 154(b) by 161 days.

(21) Appl. No.: 15/528,289

(22) PCT Filed: Nov. 24, 2015

(86) PCT No.: PCT/EP2015/077517
§ 371 (c)(1),
(2) Date: May 19, 2017

(87) PCT Pub. No.: WO2016/083384
PCT Pub. Date: Jun. 2, 2016

(65) Prior Publication Data
US 2017/0312443 A1    Nov. 2, 2017

(30) Foreign Application Priority Data
Nov. 24, 2014 (EP) ..................................... 14306863

(51) Int. Cl.
*A61M 5/32* (2006.01)
*A61M 5/315* (2006.01)
(Continued)

(52) U.S. Cl.
CPC .... *A61M 5/31551* (2013.01); *A61M 5/31536* (2013.01); *A61M 5/31553* (2013.01);
(Continued)

(58) Field of Classification Search
CPC .. A61M 2005/3125; A61M 2005/3126; A61M 2005/3154; A61M 5/31541; A61M 5/31553
See application file for complete search history.

(56) References Cited

U.S. PATENT DOCUMENTS

| 7,857,791 B2 * | 12/2010 | Jacobs | .............. A61M 5/31555 |
| | | | 604/224 |
| 2007/0191784 A1 * | 8/2007 | Jacobs | .............. A61M 5/31555 |
| | | | 604/224 |
| 2014/0350478 A1 * | 11/2014 | Hansen | ................... A61M 5/20 |
| | | | 604/189 |

FOREIGN PATENT DOCUMENTS

| JP | 2007-530240 | 11/2007 |
| JP | 2007-530241 | 11/2007 |

(Continued)

OTHER PUBLICATIONS

International Search Report and Written Opinion in International Application No. PCT/EP2015/077517, dated Mar. 14, 2016, 8 pages.
(Continued)

*Primary Examiner* — William R Carpenter
(74) *Attorney, Agent, or Firm* — Fish & Richardson P.C.

(57) ABSTRACT

A dose setting mechanism comprising a first element and a second element; the first element being moveable with respect to the second element; the first element and the second element being coupled by a ratchet mechanism allowing motion of the first element with respect to the second element from a first position to a second position only in a first direction while preventing motion in a second
(Continued)

direction that is opposite to the first direction; once passing the second position, the first element being moveable with respect to the second element in the first direction and in the second direction.

14 Claims, 11 Drawing Sheets

(51) Int. Cl.
    *A61M 5/31* (2006.01)
    *A61M 5/24* (2006.01)
    *A61M 5/20* (2006.01)

(52) U.S. Cl.
    CPC .... *A61M 5/31558* (2013.01); *A61M 5/31571* (2013.01); *A61M 5/31583* (2013.01); *A61M 5/31585* (2013.01); *A61M 5/32* (2013.01); *A61M 5/20* (2013.01); *A61M 5/31541* (2013.01); *A61M 2005/2407* (2013.01); *A61M 2005/3125* (2013.01); *A61M 2005/3126* (2013.01); *A61M 2005/3154* (2013.01); *A61M 2202/04* (2013.01); *A61M 2205/581* (2013.01); *A61M 2205/582* (2013.01)

(56) References Cited

FOREIGN PATENT DOCUMENTS

| | | | |
|---|---|---|---|
| JP | 2009-507581 | 2/2009 | |
| WO | WO 2005/097233 | 10/2005 | |
| WO | WO 2005/097240 | 10/2005 | |
| WO | WO 2012/049140 | 4/2012 | |
| WO | WO-2013098194 A2 * | 7/2013 | .............. A61M 5/20 |

OTHER PUBLICATIONS

International Preliminary Report on Patentability in International Application No. PCT/EP2015/077517, dated May 30, 2017, 6 pages.

* cited by examiner

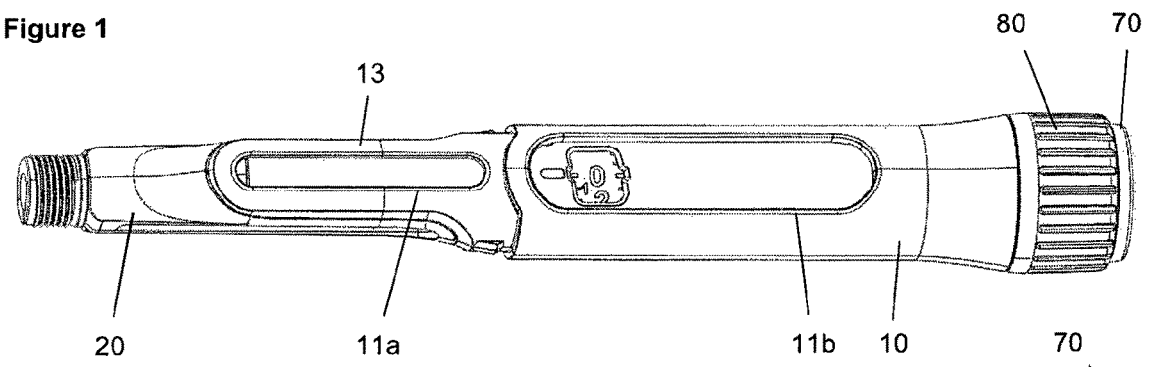
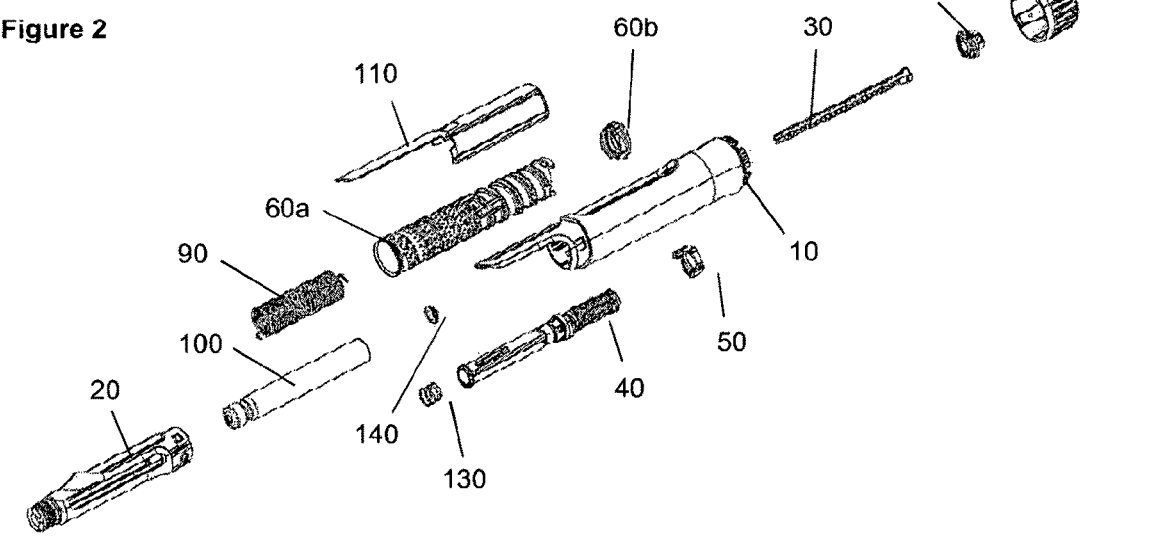
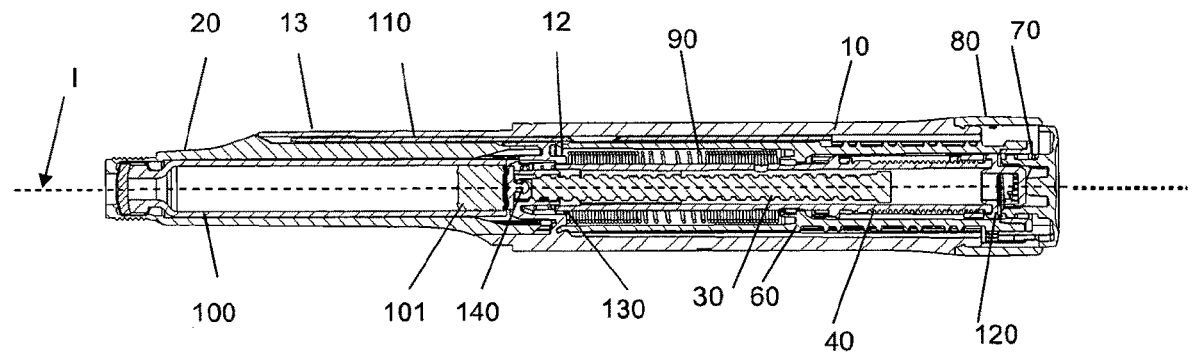

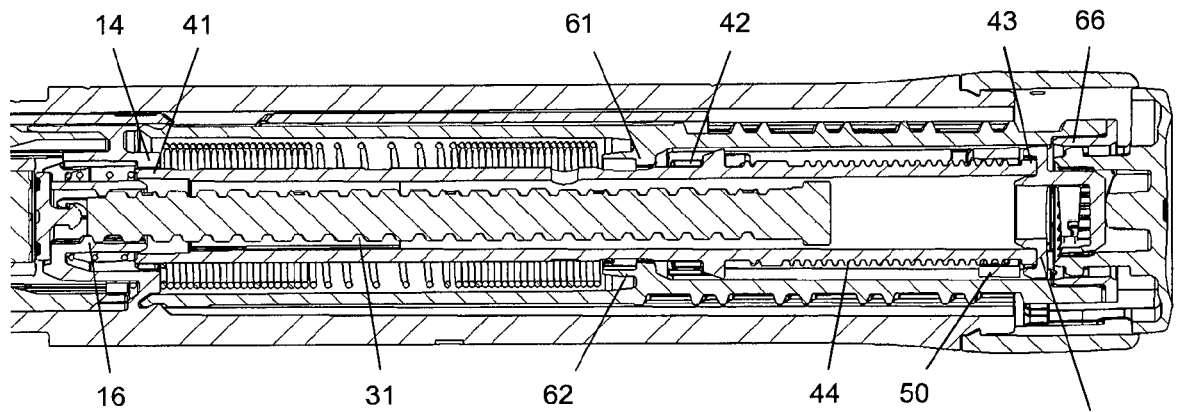
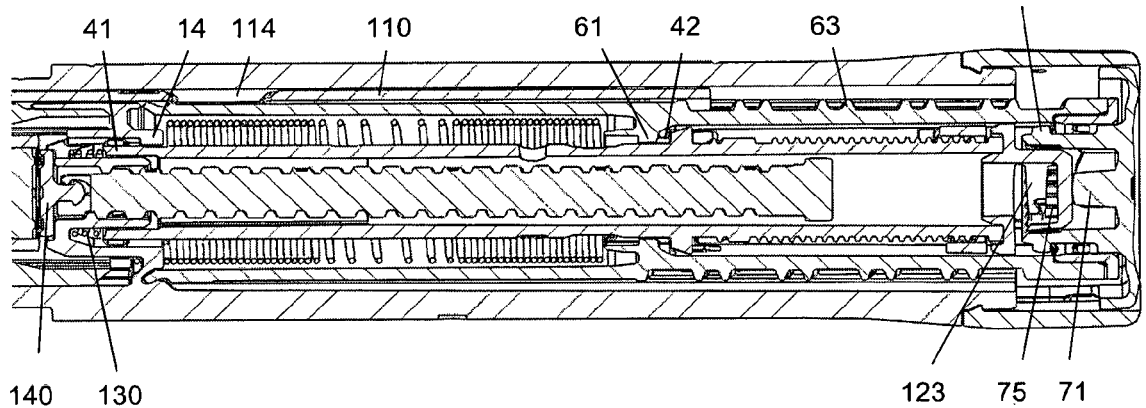
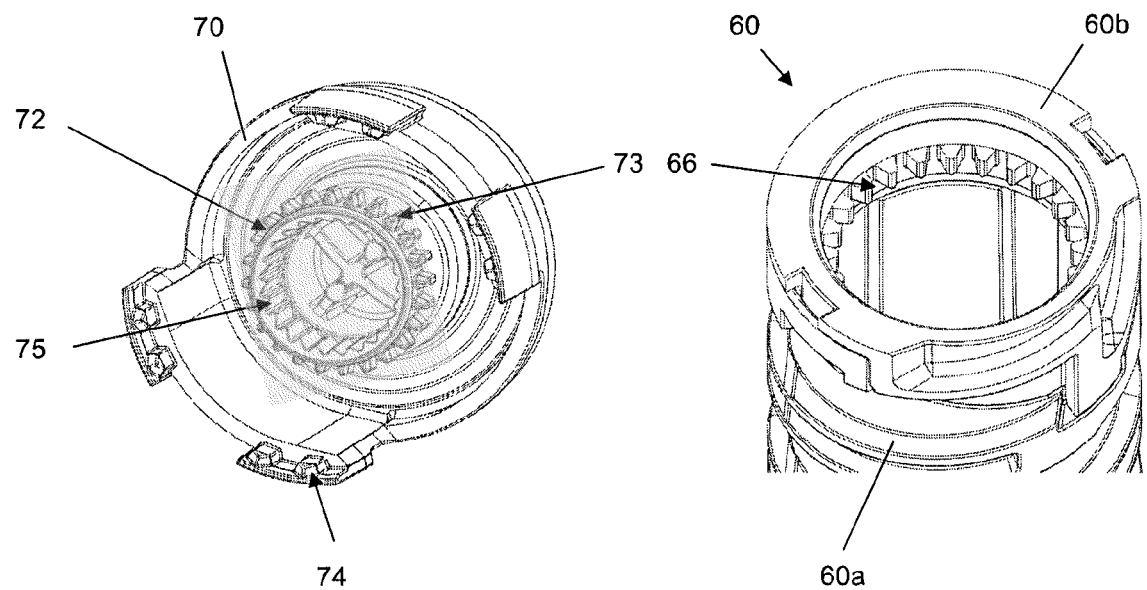

Figure 9
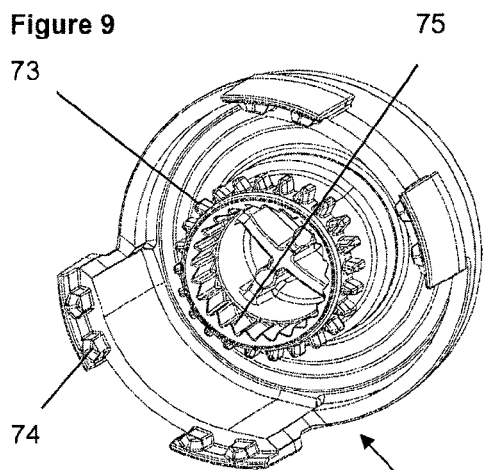 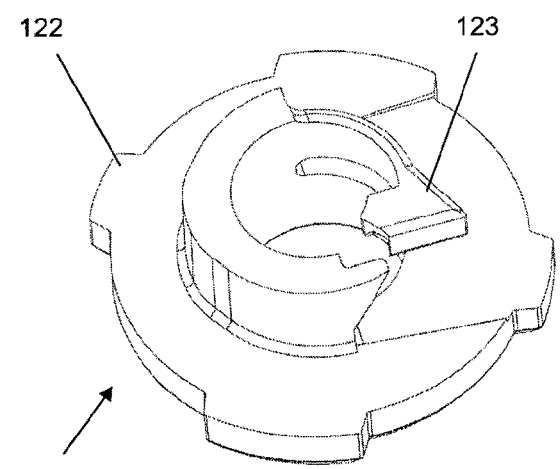
Figure 10
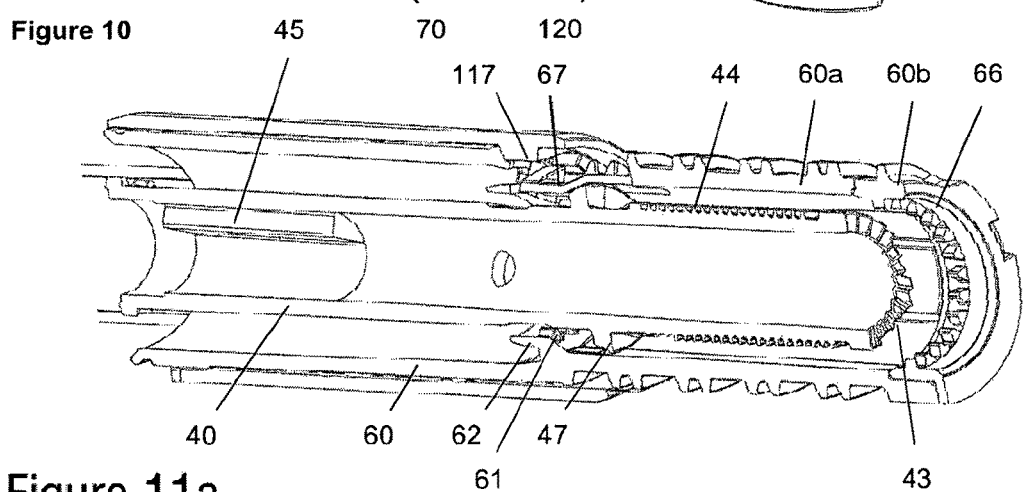
Figure 11a
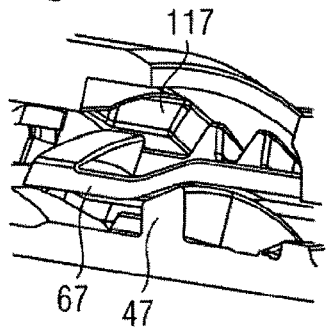
Figure 11b
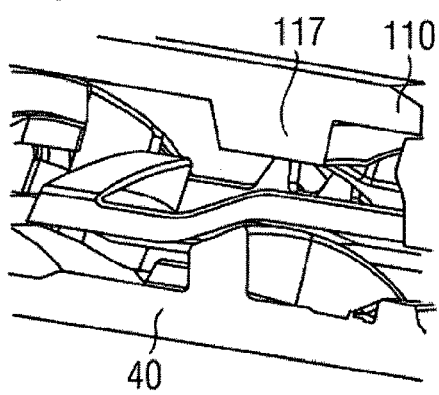
Figure 11c
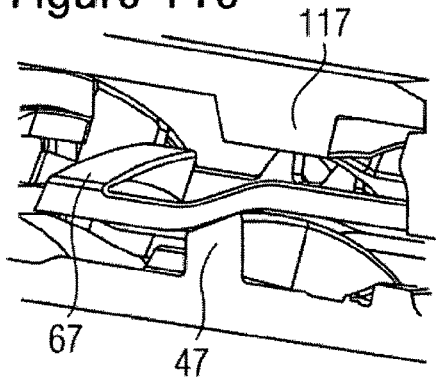

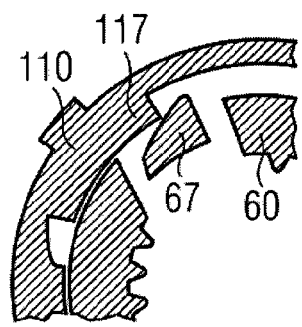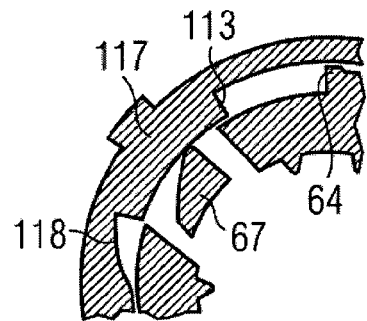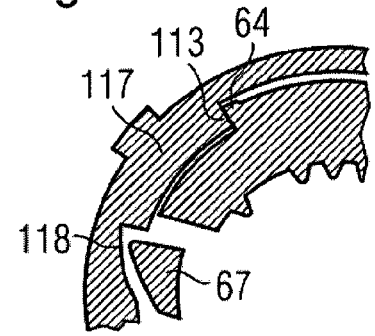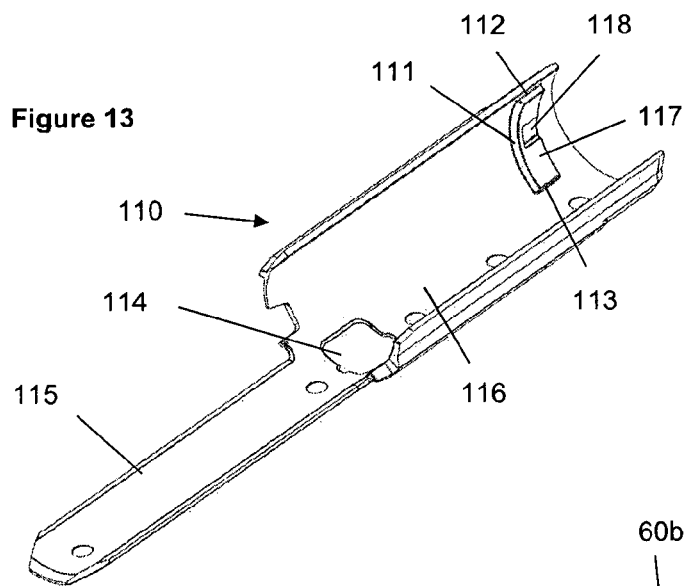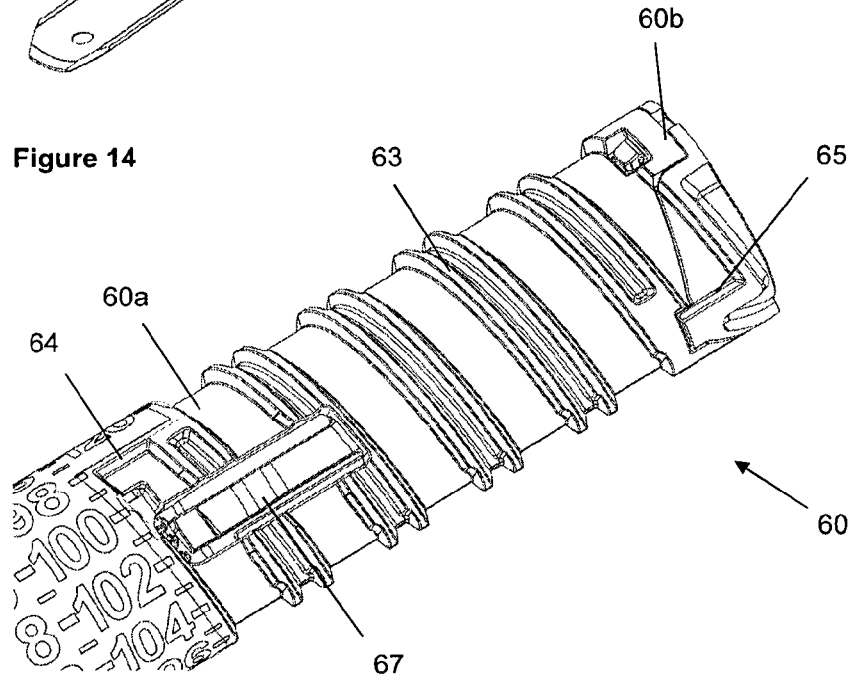

Figure 15
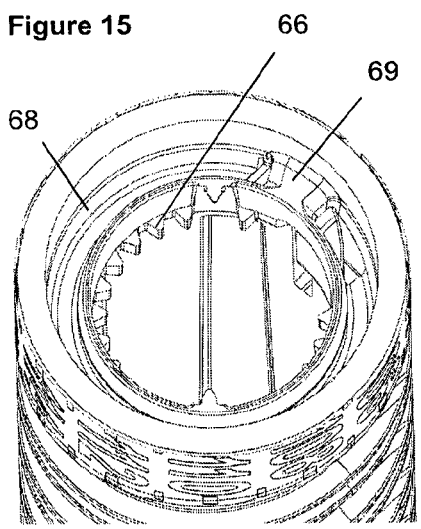
Figure 16
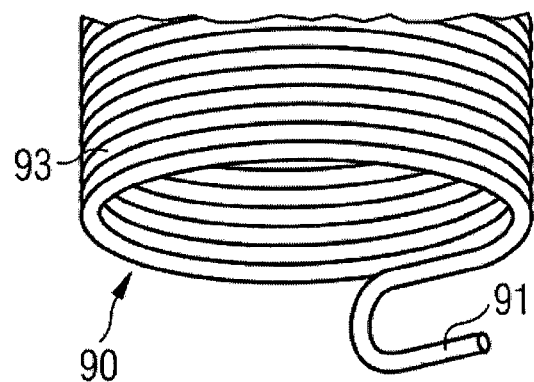
Figure 17a
Figure 17b
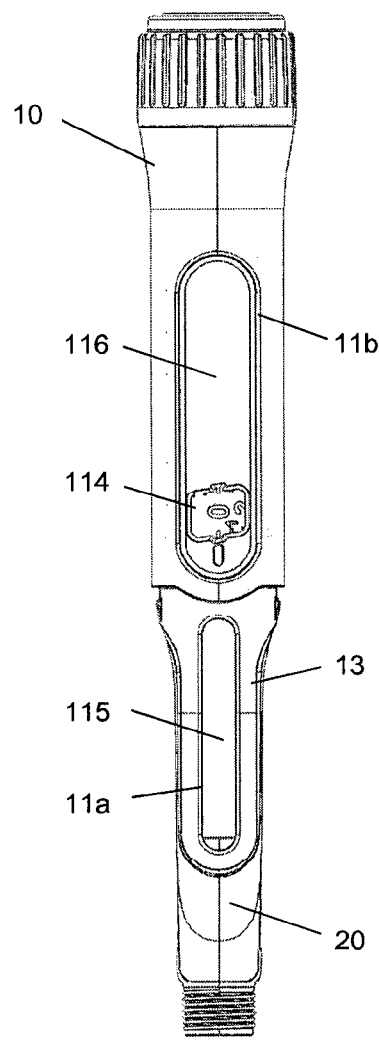
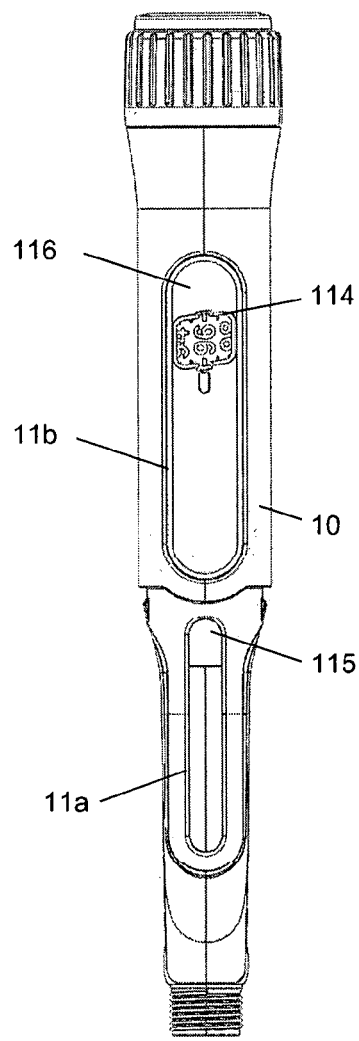

Figure 21
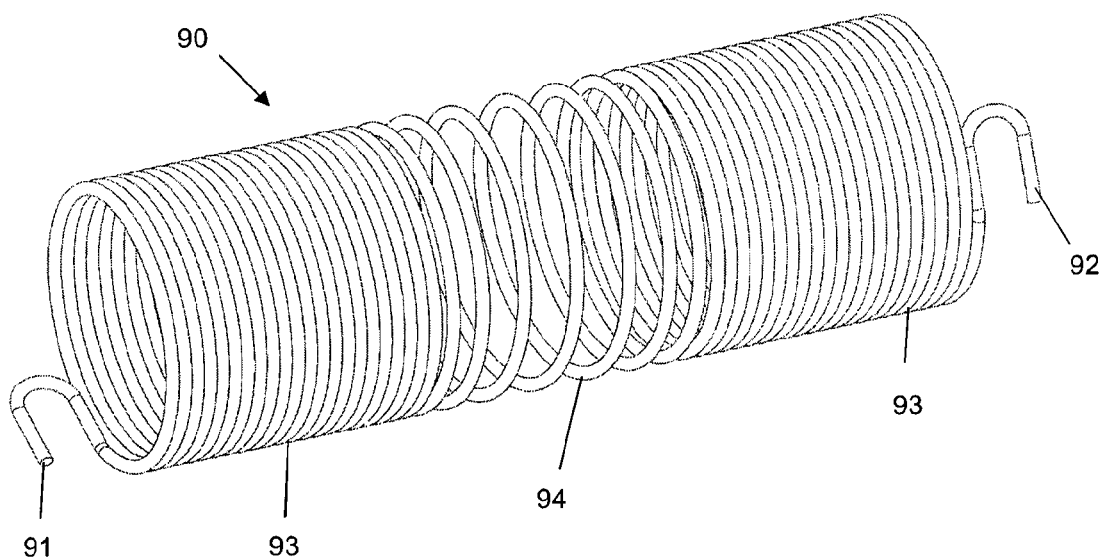
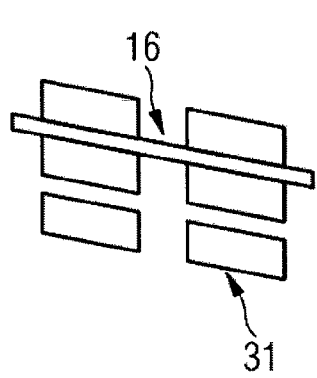
Figure 22a
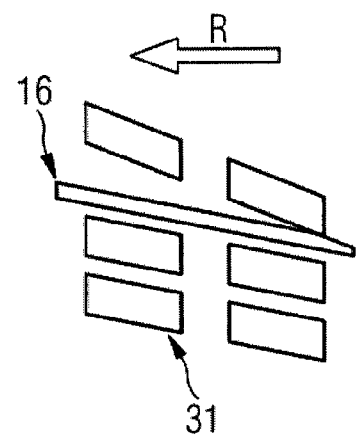
Figure 22b
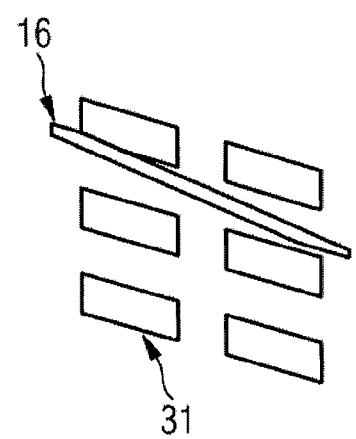
Figure 22c

DOSE SETTING MECHANISM AND DRUG DELIVERY DEVICE WITH RATCHET MECHANISM

CROSS-REFERENCE TO RELATED APPLICATIONS

This application is a U.S. National stage application under 35 USC § 371 of International Application No. PCT/EP2015/077517, filed on Nov. 24, 2015, which claims priority to European Patent Application No. 14306863.3, filed on Nov. 24, 2014, the entire contents of which are incorporated herein by reference.

TECHNICAL FIELD

The present disclosure is generally directed to a dose setting mechanism for setting a minimum dose and a drug delivery device suitable for selecting and dispensing a number of user-variable doses of a medicament, the drug delivery device comprising the dose setting mechanism for setting a minimum dose.

BACKGROUND

Drug delivery devices may have application where regular injection by persons without formal medical training is necessary. This is increasingly common among patients having diabetes where self-treatment enables such patients to conduct effective management of their disease. In practice, such a drug delivery device allows a user to individually select and dispense a number of user-variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. Some embodiments are applicable for both types of devices, i.e. for disposable devices as well as for reusable devices.

A pen-type drug delivery device, or pen delivery device, is a common type of a drug delivery device for liquid drug delivery. Pen delivery devices (so named because they often resemble an enlarged fountain pen) generally comprise three primary elements: a cartridge section that includes a cartridge often contained within a housing or holder; a needle assembly connected to one end of the cartridge section; and a dosing and delivery section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other end. The needle assembly may typically be a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

A further differentiation of drug delivery device types refers to the drive mechanism: There are devices which are manually driven, e.g. by a user applying a force to an injection button, devices which are driven by a spring or the like and devices which combine these two concepts, i.e. spring-assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. Some embodiments are applicable for both types of drive mechanisms.

The dosing section or dose setting mechanism is typically the portion of the pen device that is used to set a dose. Alternative terms are selecting or dialing a dose. During an injection, a spindle or piston rod contained within the dose setting mechanism presses against the bung or stopper of the cartridge. This force causes the medication contained within the cartridge to be injected through an attached needle assembly. After an injection, the needle assembly is usually removed and discarded.

The dose setting mechanism usually includes a component that moves during dose setting in dependence on the desired dose in one direction; then, during dose delivery, it return to its initial position. The dose may be selected and set between a zero dose, 0 U, and a maximum dose. An advantage of some embodiments may be that the dose setting mechanism is suitable for setting a minimum dose size, which is larger than zero, ensuring that the user cannot dispense less medicament than required.

SUMMARY

The dose setting mechanism comprises a first element and a second element; the first element being moveable with respect to the second element, preferably during dose setting. The first element and the second element are coupled by a ratchet mechanism allowing motion of the first element with respect to the second element from a first position to a second position only in a first direction, while preventing motion in a second direction that is opposite to the first direction. Once passing the second position, the first element is moveable with respect to the second element in the first direction and in the second direction. In other words, after reaching the second position or beyond the second position, the first element is moveable in the first and second direction.

The first element may be moveable with respect to the second element during dose setting and dispense. In one embodiment, the first element and the second element is coupled by a ratchet allowing motion of the first element with respect to the second element from a first position to a second position only in a first direction during dialing while preventing motion in a second direction that is opposite to the first direction during dispense. Alternatively, the ratchet is designed so it prevents motion during dialing but allows it during dispense. Motion into the second direction may be prevented during dialing.

Back to the dose setting mechanism mentioned above, the first element of the dose setting mechanism may be a component of the dose setting mechanism that moves in the first direction with respect to another component of the dose setting mechanism, which is the second element, during setting. The first element moves backwards in the opposite, second direction to its initial position during drug delivery. In one embodiment, the first element may be moved in the second direction during a dose correction mode, which allows the set dose to be reduced before delivery, once the first element has passed the second position.

The first position corresponds to an initial position. In other words, no dose is set. The second position corresponds to setting the minimum dose. In other words, a lesser dose cannot be set and delivered.

Such a dose setting mechanism may be comprised by different types of drug delivery devices.

The advantage of being able to set a minimum dose is that the drug delivery device can be used for medicaments in which it has been determined that a minimum dose is required to achieve the required efficacy, thus avoiding the issue of user error or misuse. The ability to set a minimum dispense quantity can also be combined with a maximum dose stop, so that the drug delivery device can limit the user to a pre-determined range, or alternatively to a single fixed dose value.

The minimum dose setting mechanism can be used within a pen injector drug delivery device for the delivery of variable, user-selectable doses of medicament into the body by means of a needle. It may be used for the delivery of a range of fluid medicaments e.g. insulin, GLP-1 or heparin.

The ratchet mechanism may comprise a ratchet feature including a multitude of teeth that is comprised by one of the first element and the second element, and a pawl that is comprised by the other one of the first element and the second element. The pawl is moveable along the multitude of teeth when the first element moves with respect to the second element in the first direction.

The ratchet mechanism is a mechanical device that allows continuous linear or rotary motion in only one direction while preventing motion in the opposite direction.

The ratchet mechanism comprises a ratchet feature, which may be a round gear or linear rack with teeth, and a pivoting, spring-loaded or elastically deformable arm called a pawl that engages the teeth. The teeth are usually uniform but asymmetrical, with each tooth having a moderate slope on one edge and a much steeper slope on the other edge.

When one of the components is moving in the unrestricted direction, the pawl easily slides up and over the gently sloped edges of the teeth, with a spring or elastic restoring force forcing it into the depression between the teeth as it passes the tip of each tooth. When the respective component moves in the opposite direction, however, the pawl will catch against the steeply sloped edge of the first tooth it encounters, thereby locking it against the tooth and preventing any further motion in that direction.

It should be mentioned that the ratchet mechanism can only stop backward motion at discrete points, i.e., at tooth boundaries. In other words, a ratchet mechanism does allow a limited amount of backward motion. This backward motion, which is limited to a maximum distance equal to the spacing between the teeth, is called backlash. Preventing motion in the second direction means preventing movement over the tips of the teeth, but may include backlash.

The dose setting mechanism has a longitudinal axis which may correspond to the axis of the drug delivery device. In one embodiment, the teeth extend axially and the pawl is deflectable axially when sliding along the multitude if teeth. In this case, the pivoting movement of the pawl may cause a rather axial deflection of the pawl's tip with respect to the axis.

In an alternative embodiment, the teeth extend radially and the pawl is deflectable radially when sliding along the multitude of teeth. In this case, the pivoting movement of the pawl may cause a rather radial deflection of the pawl's tip with respect to the axis.

In one embodiment, the multitude of teeth is arranged in a line between a first pawl position and a second pawl position; the pawl being moveable along the multitude of teeth from the first pawl position to the second pawl position when the first element moves with respect to the second element from the first position to the second position. The multitude of teeth allows only movement in the first direction until the minimum dose is set.

Preferably, the pawl is moveable along a return path from the second pawl position to the first pawl position, bypassing the multitude of teeth, once the first element has passed the second position. Providing the return path allows movement of the first element and the pawl into their initial positions during dose delivery.

In one embodiment, the ratchet mechanism comprises a first guiding means for guiding the pawl from the first pawl position towards the multitude of teeth when the first element moves with respect to the second element in the first direction. A second guiding means allows guiding the pawl from a second position into the return path when the first element moves with respect to the second element in the second direction. These guiding means may be formed as inclined edges which guide the pawl into the desired direction when moving towards and along the respective edges.

In one embodiment, the multitude of teeth is arranged along a bottom side of the ratchet feature. The return path runs along a top side of the ratchet feature which is opposite to the bottom side. The first and second guiding means are arranged on opposite sides. During setting, the pawl slides from its initial position along the first guiding means and the multitude of teeth. During delivery, the pawl is guided by the second guiding means onto the top of the ratchet feature, sliding along it back to the initial position.

The first element may serve as a dose setting member, which moves during dose setting; moving backwards initiates the movement of a piston, thereby delivering the set dose.

In one embodiment, the dose setting member comprises numbers on the outer surface, the numbers indicating the set dose. In the case of a sleeve-shaped dose setting member such a component may be considered as a number sleeve. The number sleeve is marked with a sequence of numbers to denote the dialed dose of medicament.

In one embodiment, the first element comprises a sleeve-shaped main body that is coupled to the second element by a threaded connection, which allows rotational movement of the elements with respect to each other.

The second element may serve as a gauge element defining a zero dose position, a minimum dose position and a maximum dose position together with the first element, the zero dose position being defined if the first element is in the first position; the minimum dose position being defined when if first element is in the second position, the maximum dose position is defined when the first element reaches a position beyond which no further movement in the first direction is possible. The interaction of the gauge element and the first element, which is preferably a dose setting member, allows to set variable doses between the minimum dose value and the maximum dose value.

The dose setting mechanism may comprise a maximum dose stop which prevent further movement of the first element in the first direction when the first element engages with the maximum dose stop. Such a dose stop may be formed as a stop angle or edge. In one embodiment, the sleeve-shaped first element engages with its maximum dose abutment on the maximum dose abutment of the gauge element if the user continues to increase the selected dose until the maximum dose limit is reached. This prevents further rotation of the first element.

The minimum dose setting mechanism of the drug delivery device may be formed by incorporating a ratchet feature and a flexible arm with a boss, which serve as pawl, onto a threaded component that rotates during dialing and a corresponding component engaged with the thread and prevented from free rotation in at least one of its axial positions.

This mechanism will allow a minimum dose size to be set, and can be used in combination with the maximum dose stop to provide a range of permissible doses or even a single fixed dose value.

The dose setting mechanism may be comprised by a drug delivery device. Such a drug delivery device may comprise a housing and a dose selector operable to set a dose by rotation relative to the housing. The rotatable first element is arranged within the housing such that at least a portion of the first element is visible through an aperture in the housing. The second element is interposed between the housing and the first element and is in threaded engagement with the first element such that rotation of the first element causes an axial displacement of the second element. A piston rod is coupled to the housing and to a drive sleeve such that rotation of the drive sleeve relative to the housing causes the piston rod to translate relative to the housing.

The first element may be the dose setting member. The second element may be the gauge element.

The gauge element may have a second aperture, which is positioned with respect to the first aperture of the housing such that at least a part of the number sleeve is visible through the first and second apertures or windows. The gauge element may be axially guided within the housing and in threaded engagement with the number sleeve such that rotation of the number sleeve causes an axial displacement of the gauge element.

The position of the gauge element may thus be used to identify the actually set and/or dispensed dose. Different colors of sections of the gauge member may facilitate identification of the set and/or dispensed dose without reading numbers, symbols or the like on a display. As the gauge element is in threaded engagement with the number sleeve, rotation of the number sleeve causes an axial displacement of the gauge element relative to the number sleeve and relative to the housing. The gauge element may have the form of a shield or strip extending in the longitudinal direction of the device. As an alternative, the gauge element may be a sleeve. In an embodiment, the number sleeve is marked with a sequence of numbers or symbols and the gauge element comprises an aperture. With the number sleeve located radially inwards of the gauge element, this allows that at least one of the numbers or symbols on the number sleeve is visible through the aperture. In other words, the gauge element may be used to shield or cover a portion of the number sleeve and to allow only a limited portion of the number sleeve to be viewed. This function may be in addition to the gauge element itself being suitable for identifying or indicating the actually set and/or dispensed dose.

The drug delivery device may comprise a cartridge containing a medicament. The terms "medicament" and "drug", as used herein, mean a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group-Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTIONS OF THE FIGURES

Non-limiting, exemplary embodiments will now be described with reference to the accompanying drawings, in which:

FIG. 1 shows a top view of the drug delivery device in the minimum dose position;

FIG. 2 shows an exploded view of the components of the device of FIG. 1;

FIG. 3 shows a sectional view of the device of FIG. 1;

FIG. 4a shows an enlarged sectional view of a detail of the device of FIG. 1 in the dose setting mode;

FIG. 4b shows an enlarged sectional view of a detail of the device of FIG. 1 in the dose dispensing mode;

FIG. 5 shows an interface between the number sleeve and the button of the device of FIG. 1;

Figure 7A:
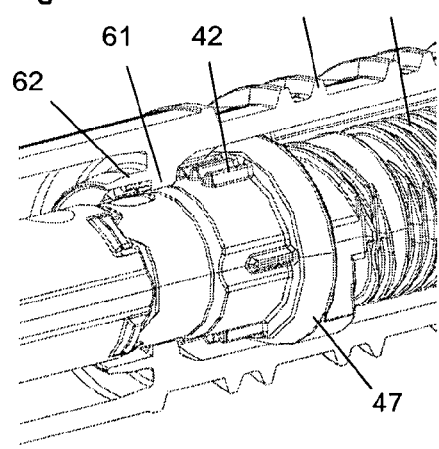
Figure 8:
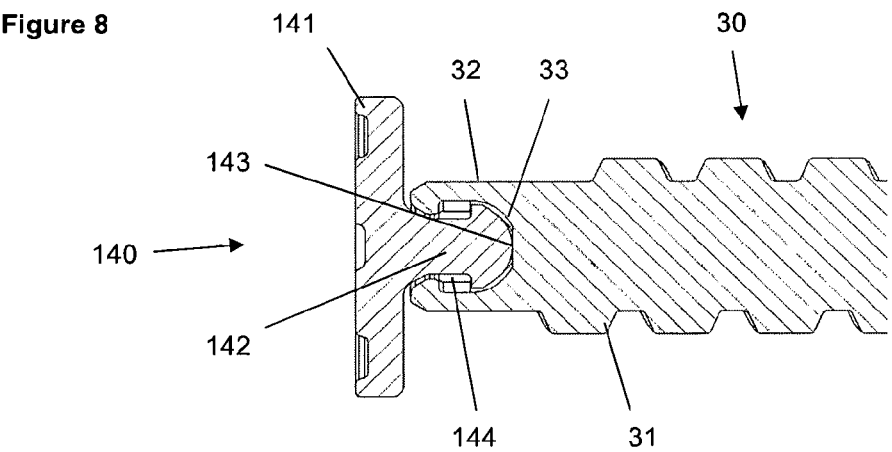
Figure 18:
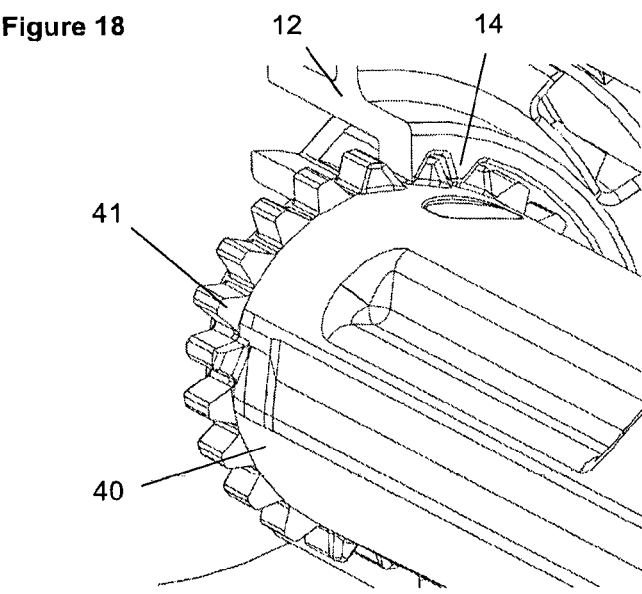
Figure 19:
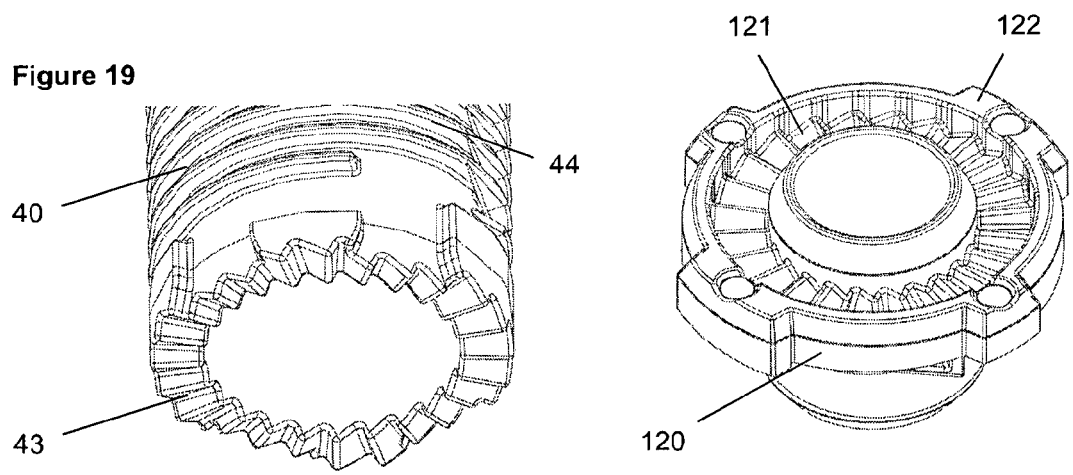
Figure 20:
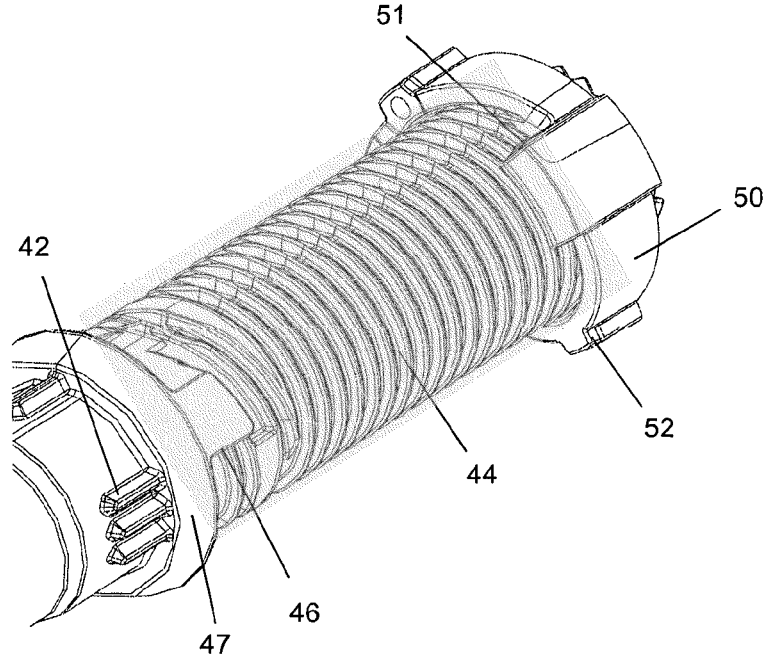

FIGS. 7a, b show an interface between the number sleeve and the drive sleeve of the device of FIG. 1 in the dose setting mode and in the dose dispensing mode;

FIG. 8 shows an interface between the piston rod and a bearing of the device of FIG. 1;

FIG. 9 shows an interface between the clutch plate and the button of the device of FIG. 1;

FIG. 10 shows in a sectional view the components of an end of dose clicker of the device of FIG. 1;

FIGS. 11 a-c show in enlarged views the sequence of generating a click at the end of dose dispensing of the device of FIG. 1;

FIGS. 12a-c show in enlarged sectional views the sequence of generating a click at the end of dose dispensing of the device of FIG. 1;

FIG. 13 shows the gauge element of the device of FIG. 1;

FIG. 14 shows a portion of the number sleeve of the device of FIG. 1;

FIG. 15 shows a further portion of the number sleeve of the device of FIG. 1;

FIG. 16 shows a portion of the drive spring of the device of FIG. 1;

FIGS. 17a, b show top views of the device of FIG. 1 with 0 units dialed and with 96 units dialed;

FIG. 18 shows an interface between the housing and the drive sleeve of the device of FIG. 1;

FIG. 19 shows an interface between the clutch plate and the drive sleeve of the device of FIG. 1;

FIG. 20 shows a last dose mechanism of the device of FIG. 1;

FIG. 21 shows the torsion spring of the device of FIG. 1; and

FIGS. 22a-c show different embodiments of the threads between the piston rod and the housing of the device of FIG. 1.

Figure 23:
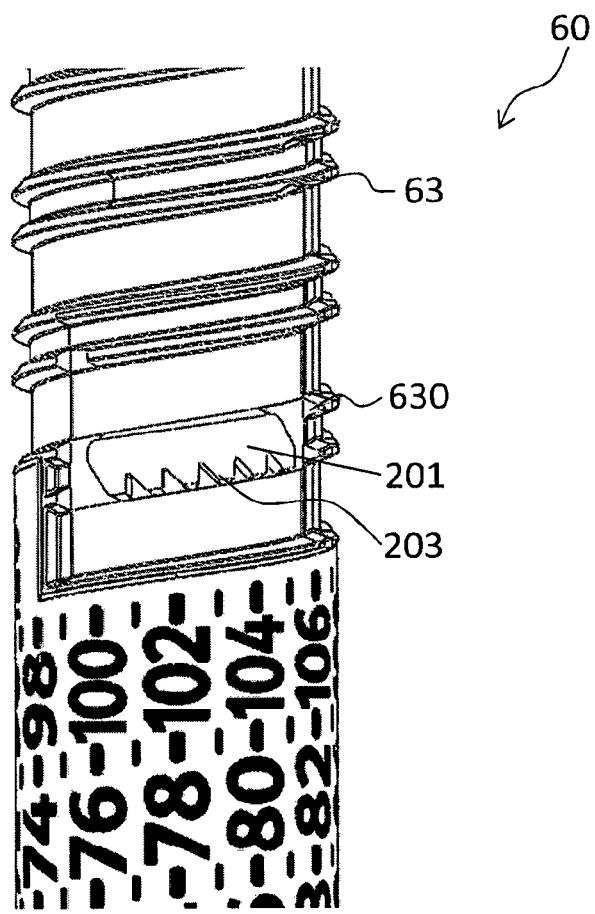

FIG. 23 shows an embodiment of a number sleeve comprising a ratchet feature.

Figure 24:
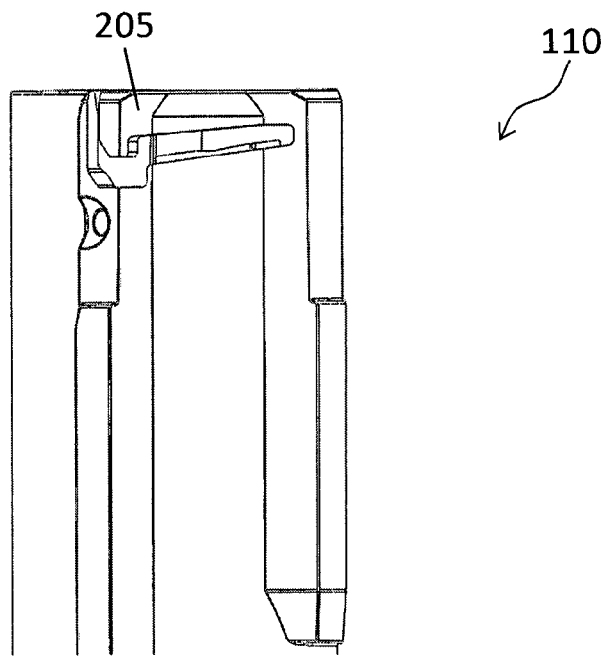

FIG. 24 shows an embodiment of the gauge element comprising a flexible arm.

Figure 25:
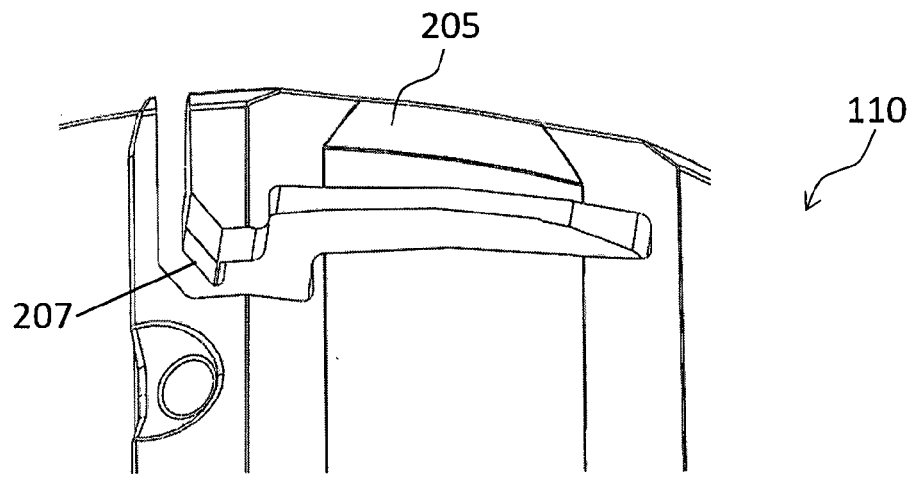

FIG. 25 shows a proximal portion of the gauge element of FIG. 24.

Figure 26:
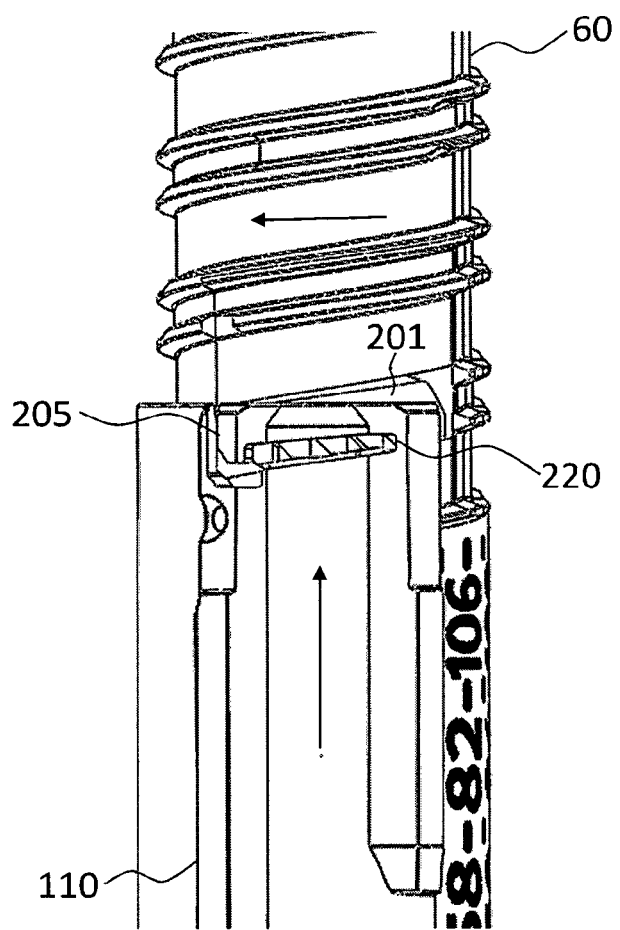

FIG. 26 shows the number sleeve of FIG. 23 and the gauge element of FIGS. 24 and 25 combined.

Figure 27:
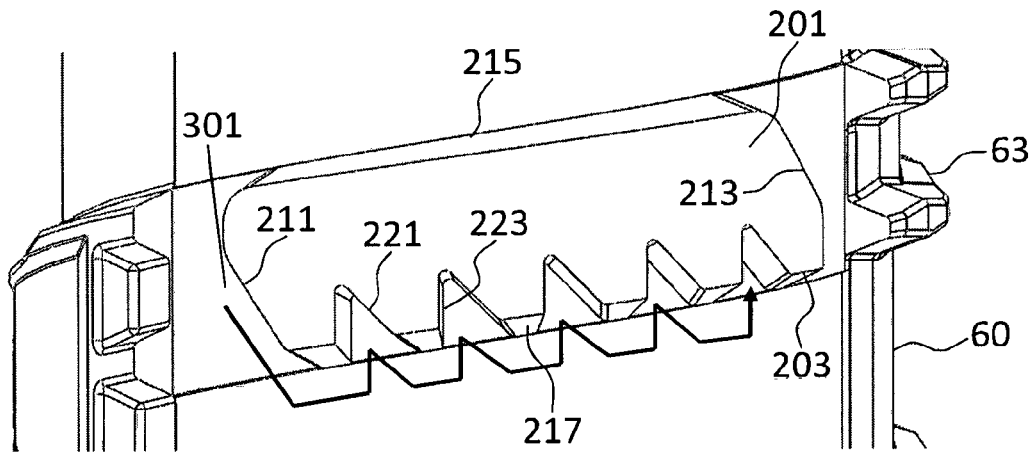
Figure 28:
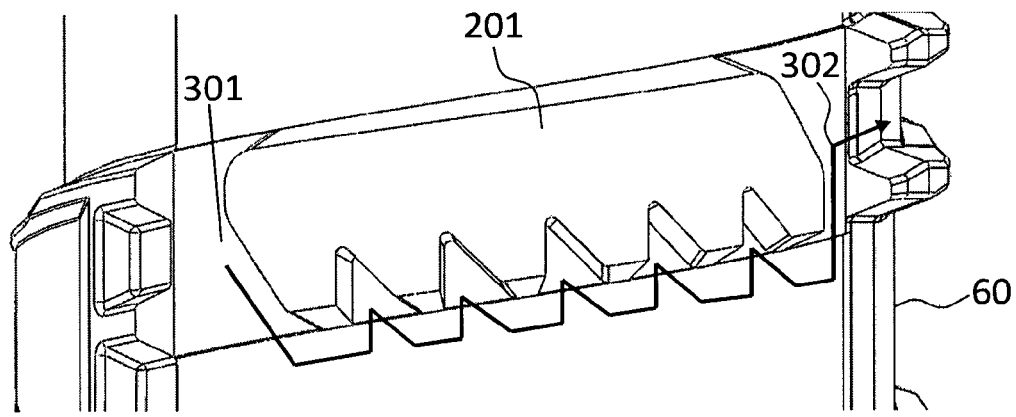
Figure 29:
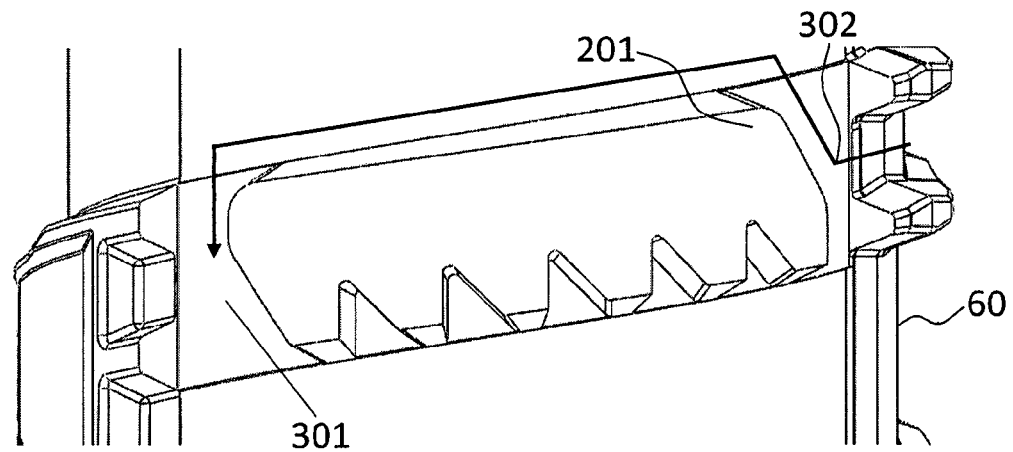

FIGS. 27-29 show different paths of a boss along the ratchet feature of FIGS. 23 and 26.

DETAILED DESCRIPTION

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element having a proximal end with an enlarged diameter. The housing 10 provides location for the liquid medication cartridge 100 and cartridge holder 20, windows 11a, 11b for viewing the dose number on the number sleeve 60 and the gauge element 110, and a feature on its external surface, e.g. a circumferential groove, to axially retain the dose selector 80. A flange-like or cylindrical inner wall 12 comprises an inner thread engaging the piston rod 30. The housing 10 further has at least one internal, axially orientated slot or the like for axially guiding the gauge element 110. In the embodiment shown in the Figures, the distal end is provided with an axially extending strip 13 partly overlapping cartridge holder 20. The Figures depict the housing 10 as a single housing component. However, the housing 10 could comprise two or more housing components which may be permanently attached to each other during assembly of the device.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the inner wall 12 of housing 10. The lead screw 30 is an elongate member with an outer thread 31 (FIG. 3) engaging the corresponding thread of the inner wall 12 of housing 10. The thread 31 may have a large lead-in, for example a wedge shape form, at its distal end to engage a corresponding housing thread form on the first rotation. The interface comprises at least one longitudinal groove or track and a corresponding protrusion or spline 45 of the driver 40. At its distal end, the lead screw 30 is provided with an interface for clip attachment of the bearing 140. In the present embodiment, this interface comprises two clip arms 32 extending in the distal direction defining an insertion space between them for insertion of a bearing 140 interface. As an alternative, the interface may comprise only one single clip arm extending more than 180° about the longitudinal axis, or may comprise one or several clip arms 32. The clip arm(s) 32 may have a bent form with a recessed clip portion as shown in FIG. 8. Preferably, the clip arm(s) form a cylindrical outer face having a diameter equal to or smaller than the outer diameter of the lead screw 30 at the base of the groove (flute base) of the outer thread 31. A concave contact surface 33 is provided between the clip arms 32 for abutment of a corresponding portion of bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

A splined tooth interface with the housing 10 prevents rotation of the drive sleeve 40 during dose setting. This interface which is shown in FIG. 18 in detail comprises a ring of radially extending outer teeth 41 at the distal end of drive sleeve 40 and corresponding radially extending inner teeth 14 of the housing component 10. When the button 70 is pressed, these drive sleeve 40 to housing 10 spline teeth 14, 41 are disengaged allowing the drive sleeve 40 to rotate relative to housing 10.

Figure 7B:
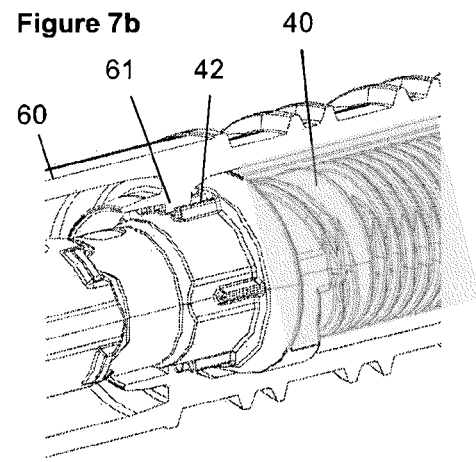

A further splined tooth interface with the number sleeve 60 is not engaged during dialing, but engages when the button 70 is pressed, preventing relative rotation between the drive sleeve 40 and number sleeve 60 during dispense. In the preferred embodiment shown in FIGS. 7a and 7b this interface comprises inwardly directed splines 61 on a flange 62 on the inner surface of the number sleeve 60 and a ring of radially extending outer splines 42 of drive sleeve 40. The corresponding splines 61, 42 are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

Preferably, the splines 61, 42 are arranged such that they are decoupled when teeth 41 of drive sleeve 40 and inner teeth 14 of housing component 10 mesh and engage when teeth 41 and inner teeth 14 disengage. In a preferred embodiment the splines 61, 42 are longer in the axial direction compared with teeth 41, 14. This allows engagement of the splines 61, 42 shortly before disengagement of teeth 41, 14. In other words, the splines 61, 42 and the teeth 41, 14 are designed and arranged such that actuation of the button 70 rotationally constrains the drive sleeve 40 to the number sleeve 60 before the drive sleeve 40 is allowed to rotate relative to housing 10. Similarly, as the button 70 is released after dose dispensing axial movement of the drive sleeve 40 first rotationally constrains the drive sleeve 40 to the housing and thereafter decouples splines 61, 42. As an alternative to the corresponding splines 61, 42 teeth may be provided. As a further alternative or in addition to splines 61, 42, drive sleeve 40 and number sleeve 60 may be rotationally coupled to each other during dose dispensing via clutch plate 120.

An interface of the drive sleeve 40 which is shown in FIG. 19 comprises a ring of ratchet teeth 43 located at the proximal end face of drive sleeve 40 and a ring of corresponding ratchet teeth 121 of clutch plate 120.

The driver 40 has a threaded section 44 providing a helical track for the nut 50 (FIG. 20). In addition, a last dose abutment or stop 46 is provided which may be the end of the thread 44 track or preferably a rotational hard stop for interaction with a corresponding last dose stop 51 of nut 50, thus limiting movement of the nut 50 on the thread 44. At least one longitudinal spline 45 engages a corresponding track of the lead screw 30. Further, the drive sleeve is provided with a ramp 47 interacting with a clicker arm 67 when the drive sleeve 40 is in its distal position during dose dispensing, i.e. when button 70 is depressed.

The last dose nut 50 is located between the number sleeve 60 and the drive sleeve 40. It is rotationally constrained to the number sleeve 60, via a splined interface (splines 52 on nut 50). It moves along a helical path relative to the drive sleeve 40, via a threaded interface (thread 44), when relative rotation occurs between the number sleeve 60 and drive sleeve 40 which is during dialing only. This is shown in FIG. 20. As an alternative, the nut 50 may be splined to the driver 40 and threaded to the number sleeve 60. In the embodiment shown in the Figures, the nut 50 is a full nut, but in alternative embodiments it may be a half nut, i.e. a component extending approximately 180° around the center axis of the device. A last dose stop 51 is provided engaging stop 46 of drive sleeve 40 when a dose is set corresponding to the remaining dispensable amount of medicament in the cartridge 100.

The dose indicator or number sleeve 60 is a tubular element as shown in FIGS. 2 and 3. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member.

For manufacturing reasons, the number sleeve 60 of the embodiment shown in the Figures comprises a number sleeve lower 60a which is rigidly fixed to a number sleeve upper 60b during assembly to form the number sleeve 60. Number sleeve lower 60a and number sleeve upper 60b are separate components only to simplify number sleeve 60 mold tooling and assembly. As an alternative, the number sleeve 60 may be a unitary component. The number sleeve 60 is constrained to the housing 10 by features towards the distal end to allow rotation but not translation. The number sleeve lower 60*a* is marked with a sequence of numbers, which are visible through the gauge element 110 and the openings 11*a*, 11*b* in the housing 10, to denote the dialed dose of medicament.

Further, the number sleeve lower 60*a* has a portion with an outer thread 63 engaging the gauge element 110. End stops 64, 65 are provided at the opposite ends of thread 63 to limit relative movement with respect to the gauge element 110.

Clutch features which have the form of a ring of splines 66 in the embodiment of FIG. 5 are provided inwardly directed on number sleeve upper 60*b* for engagement with splines 73 of the button 70 during dose setting and dose correction. A clicker arm 67 is provided on the outer surface of number sleeve 60 which interacts with the drive sleeve 40 and the gauge member 110 for generating a feedback signal. In addition, the number sleeve lower 60*a* is rotationally constrained to the nut 50 and to the clutch plate 120 via a splined interface comprising at least one longitudinal spline.

An interface for attachment of the torsion spring 90 to the number sleeve lower 60*a* comprises large lead-ins and a groove feature 68 with a pocket 69 or anchor point for receiving a first coil or hook portion of the spring. The groove 68 has an end feature in the form of a ramp that is in interference with the hook portion 91 of the spring. The design of the groove 68 is such that the spring 90 may be received within the pocket 69 without interfering with the gauge element 110.

Figure 6:
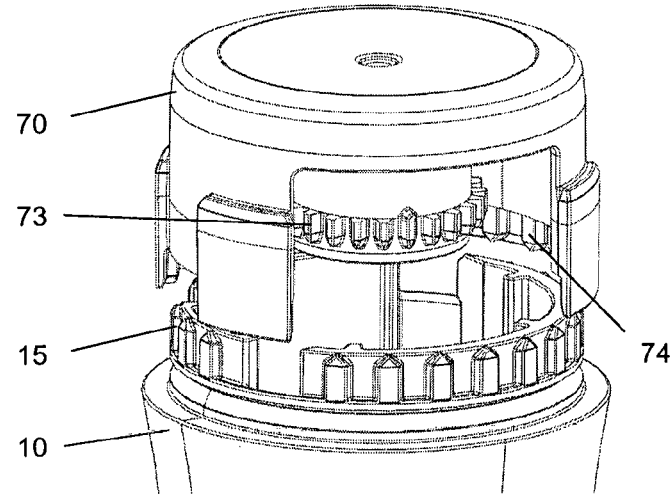
FIG. 6 shows an interface between the housing and the button of the device of FIG. 1.

The button 70 which forms the proximal end of the device is permanently splined to the dose selector 80. A central stem 71 extends distally from the proximal actuation face of the button 70. The stem 71 is provided with a flange 72 carrying the splines 73 for engagement with splines 66 of the number sleeve upper 60*b* (FIG. 5). Thus, it is also splined via splines 66, 73 (FIG. 5) to the number sleeve upper 60*b* when the button 70 is not pressed, but this spline interface is disconnected when the button 70 is pressed. The button 70 has a discontinuous annular skirt with splines 74. When the button 70 is pressed, splines 74 on the button 70 engage with splines on the housing 10 (FIG. 6), preventing rotation of the button 70 (and hence the dose selector 80) during dispense. These splines 74, 15 disengage when the button 70 is released, allowing a dose to be dialed. Further, a ring of ratchet teeth 75 is provided on the inner side of flange 72 (FIG. 9) for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. As shown in FIG. 16, the spring has a hook 91 at one end for attachment on the number sleeve 60. A similar hook end 92 is provided at the opposite end for attachment on the housing 10. The torsion spring 90 is pre-wound upon assembly, such that it applies a torque to the number sleeve 60 when the mechanism is at zero units dialed. The action of rotating the dose selector 80, to set a dose, rotates the number sleeve 60 relative to the housing 10, and charges the torsion spring 90 further.

The torsion spring 90 is formed from a helical wire with at least two different pitches. In FIG. 21, both ends are formed from 'closed' coils 93, i.e. the pitch equals the wire diameter and each coil contacts the adjacent coil. The central portion has 'open' coils 94, i.e. the coils do not contact each other.

The cartridge 100 is received in cartridge holder 20 (FIG. 3). The cartridge 100 may be a glass ampoule having a moveable rubber bung 101 at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature 111 on its inner surface which engages with the helical thread cut in the number sleeve 60 such that rotation of the number sleeve 60 causes axial translation of the gauge element 110. This helical feature on the gauge element 110 also creates stop abutments 112, 113 against the end of the helical cut in the number sleeve 60 to limit the minimum and maximum dose that can be set.

The gauge element 110 has a generally plate or band like component having a central aperture 114 or window and two flanges 115, 116 extending on either side of the aperture. The flanges 115, 116 are preferably not transparent and thus shield or cover the number sleeve 60, whereas the aperture 114 or window allows viewing a portion of the number sleeve lower 60*a*. Further, gauge element 110 has a cam 117 and a recess 118 (FIGS. 11*a*-12*c*) interacting with the clicker arm 67 of the number sleeve 60 at the end of dose dispensing.

As can be seen in FIGS. 9 and 19, the clutch plate 120 is a ring-like component. The clutch plate 120 is splined to the number sleeve 60 via splines 122. It is also coupled to the drive sleeve 40 via a ratchet interface (ratchet teeth 43, 121). The ratchet provides a detented position between the number sleeve 60 and drive sleeve 40 corresponding to each dose unit, and engages different ramped tooth angles during clockwise and anti-clockwise relative rotation. A clicker arm 123 is provided on the clutch plate 120 for interaction with ratchet features 75 of the button.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface (ratchet teeth 43, 121) is always engaged. In the 'at rest' position, it also ensures that the button splines 73 are engaged with the number sleeve splines 66, and the drive sleeve teeth 41 are engaged with teeth 14 of the housing 10.

The bearing 140 is axially constrained to the piston rod 30 and acts on the bung 101 within the liquid medicament cartridge. It is axially clipped to the lead screw 30, but free to rotate. The bearing 140 comprises a disc 141 having a stem 142 extending in the proximal direction. The stem 142 has at its proximal end a convex contact surface 143. In addition, a recessed portion 144 is provided on the stem 142. The curvature of the convex contact surface 143 and the concave contact surface 33 is chosen such that the contact diameter between the bearing 140 and lead screw 30 is small to minimize the frictional losses at this interface. The design of the clip interface between bearing 140 and lead screw 30 permits the lead screw 30 to be assembled axially, from the proximal end and through the thread engagement to the housing 10, which simplifies assembly. In addition, this design allows a simple "open and shut" mold tooling for both components.

With the device in the 'at rest' condition as shown in FIGS. 4a and 17a, the number sleeve 60 is positioned against its zero dose abutment 64, 113 with the gauge element 110 and the button 70 is not depressed. Dose marking '0' on the number sleeve 60 is visible through the windows 11b and 114 of the housing 10 and gauge element 110, respectively.

The torsion spring 90, which has a number of pre-wound turns applied to it during assembly of the device, applies a torque to the number sleeve 60 and is prevented from rotating by the zero dose abutment 64, 113. It is also possible to 'back-wind' the mechanism slightly due to an offset between the zero dose stop 64, 113 and the angular offset of the drive sleeve 40 spline teeth. This has the effect of preventing possible weepage when a dose is dialed and the zero dose abutment is disengaged.

The automated assembly of the torsion spring 90 into the number sleeve 60 can be achieved by incorporating large lead-ins and a groove feature to the number sleeve 60. As the torsion spring 90 is rotated during assembly, the hook end form 91 locates in the groove feature before engaging the anchor point in the number sleeve 60. To help to prevent the torsion spring 90 disengaging the anchor point 69 during subsequent assembly steps it is possible to create an interference between the torsion spring 90 and the number sleeve 60, or a one-way clip feature.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialed dose. The gauge element 110 has flanges 115, 116 either side of the window area 114 which cover the numbers printed on the number sleeve 60 adjacent to the dialed dose to ensure only the set dose number is made visible to the user.

A specific feature is the inclusion of a visual feedback feature in addition to the discrete dose number display typical on devices of this type. The distal end (flange 115) of the gauge element 110 creates a sliding scale through a small window 11a in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting colored component underneath. Alternatively, the revealable element may be printed with coarse dose numbers or other indices to provide more precise resolution. In addition, the gauge display simulates a syringe action during dose set and dispense.

The openings 11a, 11b in the housing 10 allow the user to view the gauge feature and number display as shown in FIGS. 17a and 17b. To reduce dust ingress and prevent the user from touching moving parts, these openings 11a, 11b are covered by translucent windows. These windows may be separate components, but in this embodiment they are incorporated into the housing 10 using 'twin-shot' molding technology. A first shot of translucent material forms the internal features and the windows 11a, 11b, and then a 'second shot' of opaque material forms the outer cover of the housing 10.

The mechanism utilizes a dose selector 80 with an increased diameter relative to the housing 10 which aids dialing although this is not a requirement of the mechanism. This feature is particularly useful (but not essential) for an auto-injector mechanism where a power supply is charged during dose setting and the torque required to turn the dose selector 80 may be higher than for a non-auto injector device.

The drive sleeve 40 is prevented from rotating as the dose is set and the number sleeve 60 rotated, due to the engagement of its splined teeth 41 with teeth 14 of the housing 10. Relative rotation must therefore occur between the clutch plate 120 and drive sleeve 40 via the ratchet interface 43, 121.

The user torque required to rotate the dose selector 80 is a sum of the torque required to wind up the torsion spring 90, and the torque required to overhaul the ratchet interface 43, 121. The clutch spring 130 is designed to provide an axial force to the ratchet interface 43, 121 and to bias the clutch plate 120 onto the drive sleeve 40. This axial load acts to maintain the ratchet teeth engagement of the clutch plate 120 and drive sleeve 40. The torque required to overhaul the ratchet 43, 121 in the dose set direction is a function of the axial load applied by the clutch spring 130, the clockwise ramp angle of the ratchet teeth 43, 121, the friction coefficient between the mating surfaces and the mean radius of the ratchet interface 43, 121.

As the user rotates the dose selector 80 sufficiently to increment the mechanism by one increment, the number sleeve 60 rotates relative to the drive sleeve 40 by one ratchet tooth. At this point the ratchet teeth 43, 121 re-engage into the next detented position. An audible click is generated by the ratchet re-engagement, and tactile feedback is given by the change in torque input required.

Relative rotation of the number sleeve 60 and the drive sleeve 40 is allowed as splines 42, 61 are disengaged during dose setting. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface 43, 121 between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface 43, 121 between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment 65 on the maximum dose abutment 112 of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment 51 with stop face 46 of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface 43, 121 between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines 74 on the button 70 engage with splines 15 on the housing 10, preventing rotation of the button 70 (and hence the dose selector 80) during dispense. As the button 70 is stationary during dispense, it can be used in the dispense clicker mechanism as shown in FIG. 9. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface 42, 61 between the drive sleeve 40 and number sleeve 60 as shown in FIGS. 7a (splines 42, 61 disengaged) and 7b (splines 42, 61 engaged), preventing relative rotation between the drive sleeve 40 and number sleeve 60 during dispense. The splined tooth interface 41, 14 between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment 64, 113 stops the mechanism.

The bearing 140 is axially clipped to the piston rod 30, but free to rotate. Since the bearing 140 is in direct contact with the bung 101, it does not rotate as the piston rod 30 rotates and advances during dose dispense. As described above, the contact diameter between the bearing 140 and piston rod 30 is small to minimize the frictional losses at this interface. The design of the piston rod 30 and bearing 140 eliminates delicate clip features or large contact diameters present on previous concepts. This embodiment also allows the piston rod 30 to be assembled axially, from the proximal end and through the thread engagement to the housing 10, which simplifies assembly.

Tactile feedback during dose dispense is provided via the compliant cantilever clicker arm 123 integrated into the clutch plate 120. This arm 123 interfaces radially with ratchet features 75 on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features 75 engage with the clicker arm 123 to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines 14, 41 between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only.

Once the delivery of a dose is stopped, by the number sleeve 60 returning to the zero dose abutment, the user may release the button 70, which will re-engage the spline teeth 14, 41 between the drive sleeve 40 and housing 10. The mechanism is now returned to the 'at rest' condition.

It is possible to angle the spline teeth 14, 41 on either the drive sleeve 40 or housing 10 so that when the button 70 is released the re-engagement of the spline teeth 14, 41 fractionally 'backwinds' the drive sleeve 40 thereby removing the engagement of the number sleeve 60 to the zero dose stop abutment on the gauge element 110. This compensates for the effect of clearances in the mechanism (for example due to tolerances) which could otherwise lead to slight advancement of the piston rod 30 and medicament dispense when the device is dialed for the subsequent dose due to the number sleeve 60 zero dose stop not restraining the mechanism and instead the restraint returning to the splines between the drive sleeve 40 and housing 10.

At the end of dose dispensing, additional audible feedback is provided in the form of a 'click', distinct from the 'clicks' provided during dispense, to inform the user that the device has returned to its zero position via the interaction of the clicker arm 67 on the number sleeve 60 with the ramp 47 on the drive sleeve 40 and the cam 117 and the recess 118 on the gauge element 110. This embodiment allows feedback to only be created at the end of dose delivery and not created if the device is dialed back to, or away from, the zero position.

FIG. 11a shows the position of the click features when the device is in the 'at rest' condition, with zero units dialed and the button 70 not depressed. It can be seen that the cam feature 117 on the gauge element 110 does not contact the clicker arm 67 on the number sleeve 60 when the button 70 is in the 'at rest' condition, so during storage or dialing the clicker arm 67 is not deflected.

During dialing, the gauge element 110 translates in the proximal direction, so the cam 117 is no longer aligned axially with the clicker arm 67. At the start of dose delivery when the drive sleeve 40 translates in the distal direction, the ramp 47 on the drive sleeve 40 pushes the clicker arm 67 radially outwards. During dose delivery, the gauge element 110 translates back in the distal direction, and towards the end of dose delivery, the clicker arm 67 contacts the cam 117 on the gauge element 110. For small doses, the cam 117 and clicker arm 67 will be in contact at the start of the dose. FIGS. 11b to 12c show the component interactions. After dose delivery, the button 70 is released and the end of dose mechanism returns to its 'at rest' position.

In FIG. 11b a dose is dialed and approximately one full dial turn is applied to number sleeve 60. Gauge element 110 is axially translated away from zero-unit position, so that cam 117 is no longer aligned axially with clicker arm 67. FIG. 11c shows the start of dispensing, when button 70 is depressed to initiate dose dispense and which causes the drive sleeve 70 to translate axially. Ramp 47 on the drive sleeve 40 pushes clicker arm 67 radially out and into radial alignment with cam 117 on the gauge element 110.

FIG. 12a shows the mechanism at the end of dose dispensing with approximately 4 units remaining. The gauge element 110 returns axially towards its zero-unit position, so that cam 117 aligns axially with clicker arm 67. Rotation of number sleeve 60 causes clicker arm 67 to contact cam 117 such that clicker arm 67 is pushed radially inwards. With approximately 2 units remaining the number sleeve 60 rotates further and clicker arm 67 follows the profile of cam 117 (FIG. 12b). This radial deflection 'charges' clicker arm 67 storing elastic energy. In FIG. 12c dispensing is completed as the number sleeve 60 reaches its zero-unit rotational position. The clicker arm 67 drops off the sharp edge of cam 117 into recess 118. Elastic energy is released causing clicker arm 67 to spring radially outwards to contact cam 117 and create a distinct 'click'.

In the principal embodiment, the lead screw 30 advances by a fixed displacement for each revolution of the drive sleeve 40. In other embodiments, the rate of displacement may vary. For example, the lead screw 30 may advance a large displacement per revolution to dispense a first amount of medicament from the cartridge 100 and then a smaller displacement per revolution to dispense the rest of the cartridge 100. This is advantageous, as it can compensate for the fact that the first dose dispensed from the cartridge 100 often has a lower volume than other doses, for a given displacement of the mechanism.

FIG. 22 shows three embodiments with the threads 16 of the housing 10 and the threads 31 of the lead screw 30 projected around the circumference. Arrow R indicates the direction of revolution of the lead screw 30 with respect to housing 10 for all three views.

View (a) shows the principal embodiment, where the pitch is equal on the housing 10 and lead screw 30, so the lead screw 30 advances a fixed amount for every revolution of the drive sleeve 40. In view (b), the first turn of thread 31 on the lead screw 30 has a large pitch, and the other turns have a small pitch. During the first revolution, the lead screw 30 displacement depends on the large pitch of the first turn of thread 31 on the lead screw 30, so it displaces a large amount per revolution. For subsequent revolutions the lead screw 30 displacement depends on the smaller pitch of the lead screw thread 31, so it displaces a smaller amount. In view (c), the housing 10 thread 16 has a larger pitch than the lead screw 30. During the first revolution, the lead screw 30 displacement depends on the pitch of the housing thread 16, so it displaces a large amount per revolution. For subsequent revolutions the lead screw 30 displacement depends on the pitch of the lead screw thread 31, so it displaces a smaller amount.

In one embodiment, the drug delivery device comprises a dose setting mechanism for setting a minimum dose size. Such a dose setting mechanism should ensure that the user cannot dispense less medicament than required.

As already described above, the drug delivery device comprises a number sleeve 60 which rotates in one direction, which is the dose setting direction, during dose setting. The number sleeve 60 rotates in the reverse direction during dispensing or correction of the set dose. The gauge element 110 engages the thread 63 on the number sleeve 60, resulting in an axial movement in the dose setting direction during setting and in the reverse direction during dispensing or correction.

The dose setting mechanism comprises a ratchet mechanism 220 including a ratchet feature 201 having a multitude of teeth 203 and a flexible pawl which may slide along the teeth 203.

FIG. 23 shows the ratchet feature 201 incorporated on the number sleeve 60. The ratchet feature 201 comprises a multitude of axially extending teeth 203 arranged in a line before the beginning 630 of a helically shaped thread-forming structure. The ratchet feature 201 including the teeth 203 are formed as a radially extending protrusion of the number sleeve 60.

FIG. 24 shows the gauge element 110 comprising a flexible arm 205 located at the proximal end of the gauge element 110. FIG. 25 shows the proximal portion of the gauge element 110 in detail.

The flexible arm 205 may be formed as an indentation or cut in the main body of the gauge element 110. Alternatively, the arm 205 may be formed by attaching it to the main body of the gauge element 110. The connection of the arm 205 and the main body forms a hinge that allows a pivoting movement. The flexibility of the material allows the deflection of the arm 205 under force and its return to the relaxed position thereafter.

The arm 205 comprises a boss 207 at the free end, which extends radially inwards towards the number sleeve 60. The boss 207 engages with the teeth 203 of the ratchet feature 201 on the number sleeve 60.

The arm 205, including the boss 207, serves as the pawl of the ratchet mechanism 220. The boss 207 interacts with the ratchet feature 201. The ratchet feature 201 is formed on the number sleeve 60 and the flexible arm 205 serving as pawl is formed on the gauge element 110.

The ratchet mechanism 220 allows linear motion in only one direction while preventing motion in the opposite direction. The teeth 203 are uniform but asymmetrical, with each tooth 203 having a moderate slope on one edge 221 and a much steeper slope on the other edge 223.

When the pawl is moving in the unrestricted direction, the pawl easily slides up and over the gently sloped edges 221 of the teeth 203, with the elasticity of the material forcing it into the depression between the teeth 203 as it passes the tip 217 of each tooth 203. When the pawl moves in the opposite direction, however, the pawl will catch against the steeply sloped 223 edge of the first tooth it encounters, thereby locking it against the tooth 203 and preventing any further motion in that direction.

Alternatively, if the steeply sloped edge 223 is steeper than the gently sloped edge 221, but not as steep as an axial edge, the ratchet mechanism 220 may permit deselecting of a dose but not dispense of a dose. During dispense, the torque on the number sleeve 60 is limited by the torsion spring 90, and may be insufficient to allow the number sleeve 60 to override the ratchet mechanism 220, which would prevent dispense. During deselection of a dose, the user applies a torque to the dose selector 80, which is transferred to the number sleeve 60. This torque may be sufficient to override the ratchet mechanism 220, allowing deselection.

The ratchet mechanism 220 has been embodied as having teeth 203 on the ratchet feature which cause the flexible arm 205 to deflect upwards and downwards in an axial motion. Alternatively, the ratchet mechanism 220 could be embodied with radially formed teeth, which would cause the flexible arm to deflect in a radial manner. Such an embodiment would still require the arm to deflect axially during dispensing or undialing to bypass the teeth. Alternatively, it would be possible to form the features in reverse, with the ratchet feature formed on the gauge element and the flexible arm and boss formed on the number sleeve.

FIG. 26 shows the gauge element 110 assembled to the number sleeve 60. The gauge element 110 is in an initial position with respect to the number sleeve 60. This position is the 0 U dialed position. In the initial position, the boss 207 on the flexible arm 205 is positioned to a first pawl position 301 which is to the left of the ratchet feature 201 in FIG. 26.

During dialing, the number sleeve 60 will rotate clockwise when viewed from above, and the gauge element 110 will move proximally. The motions are indicated by arrows in FIG. 26.

If the user dials less than the minimum allowable dose, the interaction between the ratchet feature 201 and flexible arm 205 prevents the user from dispensing. Return movement of the number sleeve 60 to the initial position is prevented. If the user dials the minimum dose or more, the flexible arm clears the ratchet features, permitting a subsequent dispense or un-dialing of the device. The gauge element 110 may have a helical feature 111 on its inner surface which engages with the helical thread cut in the number sleeve 60 such that rotation of the number sleeve 60 causes axial translation of the gauge element 110 during dialing.

FIG. 27 shows the ratchet feature 201 on the number sleeve 60 and the path of the boss 207 indicated by the arrow along the teeth 203 if the user dials less than the minimum dose.

The ratchet feature 201 has a top side 215 and a bottom side 217; the bottom side 217 includes the multitude of teeth 203. The ratchet feature 201 has a first side 211 and a second side 213 opposite to the first side 211. One side of each tooth 203 that faces the first side 211 is a gently sloped edge 221; the other side of the teeth 203 that face the second side 213 are steeply sloped 223. The tips of the teeth 203 may be round or flattened. The top side 215 of the ratchet feature 201 is rather flat. The first and second sides 211, 213 are inclined in the same direction. The first side 211 may form the gently sloped edge 221 of the first teeth.

Before dose setting, the first or initial pawl position 301 of the boss 207 is at the first side of the ratchet feature 201. The start position 301 of the boss 207 on the flexible arm 205 is indicated by the end of the arrow in FIG. 27. The arm 205 is relaxed in the start position 301. The boss 207 may move along the edges of the teeth 203 only in a single direction, since the form of the teeth 203 locks the boss 207 when moving it backwards.

If the user dials up the drug delivery device by less than the minimum dose, the boss 207 contacts the ratchet feature 201 and the flexible arm 205 is deflected downwards. The boss 207 then interacts with the teeth on the underside of the ratchet feature 201, which do not allow a reverse motion of the components, thereby preventing the user from dispensing or undialing the device. The size of the minimum dose is determined by the length of the ratchet feature 201.

If the user dials less than the minimum allowable dose, the interaction between the ratchet feature 201 and flexible arm 205 prevents the user from dispensing. If the user dials the minimum dose or more, the flexible arm clears the ratchet features, permitting a subsequent dispensing or undialing of the device.

FIG. 28 shows the path of the boss if the user dials more than the minimum dose. The path of the boss is indicated by the arrow along the teeth 203 and beyond.

After passing the multitude of teeth 203, the second pawl position 302 of the boss 207 is at the second side 213 of the ratchet feature 201 before the beginning 630 of the thread structure 63.

If the user dials up the device by the minimum dose or more, the flexible arm 205, which is initially deflected downwards as the boss 205 interacts with the teeth 203 on the ratchet feature 201, then springs proximally to its undeflected state as it passes the ratchet feature 201. It then remains undeflected as or if the number sleeve 60 continues to be rotated up to the desired dialed dose value.

After passing the ratchet feature, the number 60 may rotate back and forth with respect to the gauge element 110 which allow setting the dose and correcting the set dose.

FIG. 29 shows the path of the boss 207 during dispense or undialing. The return path of the boss 207 is indicated by the arrow.

During dispense or un-dialing, upon reaching the end of the ratchet feature 201, the flexible arm 205 will be deflected proximally above the ratchet feature 201, avoiding the teeth 203 on the bottom side 217 which would otherwise prevent motion. The boss 207 slides along the top side 215 of the ratchet feature 201 towards the initial pawl position. At this position, which is the 0 U position, a return path allows the flexible arm to spring back to its original position, ready for the next dialing event. The return path is a gap adjacent to the first side 211 of the ratchet feature 201 allowing return of the boss to its initial position, ready for subsequent dialing. This feature also ensures that the flexible arm does not unnecessarily remain in a deflected state, which could result in creep over time.

Another embodiment is possible, where a spring or other mechanism presses the arm 205 during dispensing against the top side 215 of the ratchet feature 201.

The advantage of being able to set a minimum dose is that the pen injector can be used for medicaments in which it has been determined that a minimum dose is required to achieve the required efficacy, thus avoiding this issue of user error or misuse. The ability to set a minimum dispense quantity can also be combined with a maximum dose stop, so that the pen injector can limit the user to a predetermined range, or alternatively to a single fixed dose value.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

10 housing
11a, b opening
12 flange-like inner wall
13 strip
14 teeth
15 spline
16 inner thread
20 cartridge holder
30 lead screw (piston rod)
31 outer thread
32 clip arm
33 concave contact surface
40 driver (axially movable drive sleeve)
41 teeth
42 spline
43 ratchet teeth
44 threaded section
45 spline
46 last dose stop
47 ramp
50 nut
51 last dose stop
52 spline
60 dose indicator (number sleeve)
60a number sleeve lower
60b number sleeve upper
61 spline
62 flange
63 outer thread
630 beginning of outer thread
64, 65 end stop
66 spline
67 clicker arm
68 groove
69 anchor point
70 button
71 stem
72 flange
73, 74 spline
75 ratchet teeth
80 dose selector
90 torsion spring
91, 92 hook
93, 94 coil
100 cartridge
101 bung
110 gauge element
111 helical feature
112, 113 stop
114 aperture
115, 116 flange
117 cam
118 recess
120 clutch plate
121 ratchet teeth
122 protrusion
123 clicker arm
130 clutch spring
140 bearing
141 disc
142 stem
143 convex contact surface
144 recessed portion
201 ratchet feature
203 teeth
205 arm
207 boss
211, 213 sides
215 top side
217 bottom side
220 ratchet mechanism
221, 223 edges
301 first pawl position
302 second pawl position
I longitudinal axis
R direction of revolution

The invention claimed is:

1. A dose setting mechanism comprising:
a first element and a second element, the first element being moveable with respect to the second element, the first element comprising a sleeve-shaped main body coupled to the second element by a threaded connection; and
a ratchet mechanism coupling the first element to the second element and allowing motion of the first element with respect to the second element from a first position to a second position only in a first direction while preventing motion of the first element with respect to the second element in a second direction that is opposite to the first direction,
wherein the ratchet mechanism comprises a ratchet feature including a plurality of teeth comprised by one of the first element and the second element and a pawl that is comprised by the other one of the first element and the second element,
wherein the teeth are arranged in a line between a first pawl position and a second pawl position, and the pawl is configured to move along the teeth from the first pawl position to the second pawl position when the first element moves with respect to the second element from the first position of the first element to the second position of the first element,
wherein the first element is movable with respect to the second element in the second direction from the second position of the first element to the first position of the first element only after the first element passes the second position of the first element in the first direction, and
wherein when the first element is in the second position, the pawl is beyond the plurality of teeth and the pawl is disengaged from the teeth.

2. The dose setting mechanism according to claim 1, having a longitudinal axis wherein the teeth extend axially and the pawl is deflectable axially when sliding along the teeth.

3. The dose setting mechanism according to claim 1, wherein the teeth have first edges being steeply sloped edges and second edges which are less steep edges.

4. The dose setting mechanism according to claim 1, wherein the pawl is moveable along a return path from the second pawl position to the first pawl position, bypassing the teeth, once the first element has passed the second position of the first element.

5. The dose setting mechanism according to claim 4, wherein the ratchet mechanism comprises
a first inclined side for guiding the pawl from the first pawl position towards the multitude of teeth when the first element moves with respect to the second element in the first direction;
a second inclined side for guiding the pawl from the second pawl position into the return path when the first element moves with respect to the second element in the second direction.

6. The dose setting mechanism according to claim 5, wherein the teeth are arranged along a bottom side of the ratchet feature;
the return path runs along a top side of the ratchet feature which is opposite to the bottom side; and
the first and second inclined sides are arranged opposite one another.

7. The dose setting mechanism according to claim 1, wherein the first element serves as a dose setting member.

8. The dose setting mechanism according to claim 7, wherein the dose setting member comprises numbers on an outer surface of the dose setting member, the numbers indicating a set dose.

9. The dose setting mechanism according to claim 1, wherein the second element serves as a gauge element defining a minimum dose position and a maximum dose position together with the first element, the minimum dose position is defined when the first element is in the second position of the first element, and the maximum dose position is defined when the first element reaches a position beyond which no further movement of the first element in the first direction is possible.

10. The dose setting mechanism according to claim 1, further comprising a maximum dose stop which prevents further movement of the first element in the first direction when the first element engages with the maximum dose stop.

11. The dose setting mechanism according to claim 1, wherein the threaded connection between the first element and the second element comprises a helical thread.

12. A dose setting mechanism comprising:
a first element and a second element, the first element being moveable with respect to the second element; the first element comprising a sleeve-shaped main body coupled to the second element by a threaded connection comprising a helical thread, and
a ratchet mechanism coupling the first element to the second element and allowing motion of the first element with respect to the second element from a first position to a second position only in a first direction while preventing motion of the first element with respect to the second element in a second direction that is opposite to the first direction,
wherein the ratchet mechanism comprises a ratchet feature including a plurality of teeth comprised by one of the first element and the second element and a pawl that is comprised by the other one of the first element and the second element,
wherein the teeth are arranged in a line between a first pawl position and a second pawl position, and the pawl is configured to move along the teeth from the first pawl position to the second pawl position when the first element moves with respect to the second element from the first position of the first element to the second position of the first element, and
wherein the first element is movable with respect to the second element in the second direction from the second position of the first element into the first position of the first element only after passing the second position of the first element in the first direction.

13. A drug delivery device comprising:
a dose setting mechanism comprising:
a first element and a second element, the first element being moveable with respect to the second element, the first element comprising a sleeve-shaped main body coupled to the second element by a threaded connection; and
a ratchet mechanism coupling the first element to the second element and allowing motion of the first element with respect to the second element from a first position to a second position only in a first direction while preventing motion of the first element with respect to the second element in a second direction that is opposite to the first direction,
wherein the ratchet mechanism comprises a ratchet feature including a plurality of teeth comprised by one of the first element and the second element and a pawl that is comprised by the other one of the first element and the second element,
wherein the teeth are arranged in a line between a first pawl position and a second pawl position, and the pawl is configured to move along the teeth from the first pawl position to the second pawl position when the first element moves with respect to the second element from the first position of the first element to the second position of the first element,
wherein the first element is movable with respect to the second element in the second direction from the second position of the first element to the first position of the first element only after the first element passes the second position of the first element in the first direction, wherein when the first element is in the second position, the pawl is beyond the plurality of teeth and the pawl is disengaged from the teeth;
a housing, the first element being arranged within the housing such that at least a portion of the first element is visible through an aperture in the housing, and the second element being interposed between the housing and the first element and in threaded engagement with the first element such that rotation of the first element causes an axial displacement of the second element;
a dose selector operable to set a dose by rotation relative to the housing; and
a piston rod coupled to the housing and to a drive sleeve such that rotation of the drive sleeve relative to the housing causes the piston rod to translate relative to the housing.

14. The drug delivery device of claim 13, further comprising a container containing a medicament disposed in the housing.

* * * * *